United States Patent
Benni

(10) Patent No.: US 7,313,427 B2
(45) Date of Patent: Dec. 25, 2007

(54) LASER DIODE OPTICAL TRANSDUCER ASSEMBLY FOR NON-INVASIVE SPECTROPHOTOMETRIC BLOOD OXYGENATION

(75) Inventor: Paul Benni, Middletown, CT (US)

(73) Assignee: CAS Medical Systems, Inc., Branford, CT (US)

( * ) Notice: Subject to any disclaimer, the term of this patent is extended or adjusted under 35 U.S.C. 154(b) by 0 days.

(21) Appl. No.: 11/384,615

(22) Filed: Mar. 20, 2006

(65) Prior Publication Data

US 2006/0195024 A1    Aug. 31, 2006

Related U.S. Application Data

(63) Continuation of application No. 09/951,221, filed on Sep. 14, 2001, now Pat. No. 7,047,054, which is a continuation-in-part of application No. 09/434,142, filed on Nov. 4, 1999, now abandoned.

(60) Provisional application No. 60/123,849, filed on Mar. 12, 1999, provisional application No. 60/151,319, filed on Aug. 30, 1999.

(51) Int. Cl.
*A61B 5/00* (2006.01)

(52) U.S. Cl. ...................... 600/344; 600/323

(58) Field of Classification Search .............. 600/310, 600/322, 323, 340, 344
See application file for complete search history.

(56) References Cited

U.S. PATENT DOCUMENTS

| | | |
|---|---|---|
| 3,638,640 A | 2/1972 | Shaw |
| 3,674,008 A | 7/1972 | Johnson |

(Continued)

Primary Examiner—Eric F Winakur
(74) Attorney, Agent, or Firm—O'Shea, Getz & Kosakowski, P.C.

(57) ABSTRACT

A non-invasive near infrared spectrophotometric monitoring transducer assembly includes a housing member, which is adhered directly on a patient's skin. The housing member contains a prism coupled to a flexible and lightweight single core optical light guide, which provides a means of transferring narrow spectral bandwidth light from multiple distant laser diodes of different wavelengths by use of a multi-fiber optic light combining assembly. Different wavelengths are needed to monitor the level of blood oxygenation in the patient. The assembly also contains a planar light guide mounted on the prism located in the housing member, which light guide contacts the patient's skin when the housing member is adhered to the patient's skin. The light guide controls the spacing between the prism and the patient's skin, and therefore controls the intensity of the area on the patient's skin which is illuminated by the laser light. The housing member contains a photodiode assembly, which detects the infrared light at a second location on the skin to determine light absorption. The photodiode assembly is preferably shielded from ambient electromagnetic interference (EMI) by an optically transparent EMI attenuating window. This rigid window placed over the photodiode also provides a planar interface between the assembly and the skin, improving optical coupling and stability as well as reducing the capacitive coupling between skin and the photodiode resulting in further EMI attenuation. The housing may be associated with a disposable sterile hydrogel coated adhesive envelope, or pad, which when applied to the patient's skin will adhere the housing to the patient's skin. The transducer assembly will thus be reusable, and skin-contacting part of the device, i.e., the envelope or pad can be discarded after a single use. The assembly also includes a laser safety interlock means, which is operable to turn off the laser light output in the event that the assembly accidentally becomes detached from the patient's skin.

3 Claims, 9 Drawing Sheets

U.S. PATENT DOCUMENTS

| | | | | |
|---|---|---|---|---|
| 4,105,021 A | | 8/1978 | Williams et al. | |
| 4,206,764 A | | 6/1980 | Williams | |
| 4,223,680 A | | 9/1980 | Jobsis | |
| 4,281,645 A | | 8/1981 | Jobsis | |
| 4,321,930 A | | 3/1982 | Jobsis et al. | |
| 4,380,240 A | | 4/1983 | Jobsis et al. | |
| 4,510,938 A | | 4/1985 | Jobsis et al. | |
| 4,570,638 A | | 2/1986 | Stoddart et al. | |
| 4,621,643 A | | 11/1986 | New, Jr. et al. | |
| 4,690,492 A | | 9/1987 | Beard | |
| 4,700,708 A | | 10/1987 | New, Jr. et al. | |
| 4,725,147 A | | 2/1988 | Stoddart | |
| 4,768,516 A | | 9/1988 | Stoddart et al. | |
| 4,770,179 A | | 9/1988 | New, Jr. et al. | |
| 4,805,623 A | | 2/1989 | Jobsis | |
| 4,817,623 A | | 4/1989 | Stoddart et al. | |
| 4,848,901 A | | 7/1989 | Hood, Jr. | |
| 4,865,038 A | | 9/1989 | Rich et al. | |
| 4,907,876 A | | 3/1990 | Suzuki et al. | |
| 4,913,150 A | | 4/1990 | Cheung et al. | |
| 4,942,877 A | | 7/1990 | Sakai et al. | |
| 5,054,488 A | | 10/1991 | Muz | |
| 5,057,695 A | | 10/1991 | Hirao et al. | |
| 5,058,588 A | | 10/1991 | Kaestle | |
| 5,080,098 A | | 1/1992 | Willett et al. | |
| 5,088,493 A | | 2/1992 | Giannini et al. | |
| 5,139,025 A | | 8/1992 | Lewis et al. | |
| 5,140,989 A | | 8/1992 | Lewis et al. | |
| 5,153,669 A | | 10/1992 | DeGroot | |
| 5,209,230 A | * | 5/1993 | Swedlow et al. | 600/322 |
| 5,217,013 A | | 6/1993 | Lewis et al. | |
| 5,218,962 A | | 6/1993 | Mannheimer et al. | |
| 5,226,417 A | * | 7/1993 | Swedlow et al. | 600/322 |
| 5,237,994 A | * | 8/1993 | Goldberger | 600/323 |
| 5,246,003 A | * | 9/1993 | DeLonzor | 600/344 |
| 5,251,632 A | | 10/1993 | Delpy | |
| 5,263,244 A | * | 11/1993 | Centa et al. | 600/323 |
| 5,277,181 A | | 1/1994 | Mendelson et al. | |
| 5,349,961 A | | 9/1994 | Stoddart et al. | |
| 5,353,791 A | | 10/1994 | Tamura et al. | |
| 5,421,329 A | | 6/1995 | Casciani et al. | |
| 5,465,714 A | | 11/1995 | Scheuing | |
| 5,477,853 A | | 12/1995 | Farkas et al. | |
| 5,482,034 A | | 1/1996 | Lewis et al. | |
| 5,517,987 A | | 5/1996 | Tsuchiya | |
| 5,520,177 A | | 5/1996 | Ogawa et al. | |
| 5,524,617 A | | 6/1996 | Mannheimer | |
| 5,529,065 A | | 6/1996 | Tsuchiya | |
| 5,542,421 A | | 8/1996 | Erdman | |
| 5,584,296 A | | 12/1996 | Cui et al. | |
| 5,632,273 A | | 5/1997 | Suzuki | |
| 5,661,302 A | | 8/1997 | Evans et al. | |
| 5,676,142 A | | 10/1997 | Miwa et al. | |
| 5,694,931 A | | 12/1997 | Tsuchiya | |
| 5,697,367 A | | 12/1997 | Lewis et al. | |
| 5,720,284 A | | 2/1998 | Aoyagi et al. | |
| 5,729,333 A | | 3/1998 | Osten et al. | |
| 5,746,206 A | | 5/1998 | Mannheimer | |
| 5,752,914 A | | 5/1998 | Delonzor et al. | |
| 5,758,644 A | | 6/1998 | Diab et al. | |
| 5,770,454 A | | 6/1998 | Essenpreis et al. | |
| 5,782,755 A | | 7/1998 | Chance et al. | |
| 5,795,292 A | | 8/1998 | Lewis et al. | |
| 5,803,909 A | | 9/1998 | Maki et al. | |
| 5,817,008 A | * | 10/1998 | Rafert et al. | 600/344 |
| 5,853,370 A | | 12/1998 | Chance et al. | |
| 5,879,294 A | | 3/1999 | Anderson et al. | |
| 5,902,235 A | | 5/1999 | Lewis et al. | |
| 5,987,351 A | | 11/1999 | Chance | |
| 6,192,260 B1 | | 2/2001 | Chance | |
| 6,615,065 B1 | | 9/2003 | Barrett et al. | |
| 2005/0119542 A1 | | 6/2005 | Stoddart et al. | |

* cited by examiner

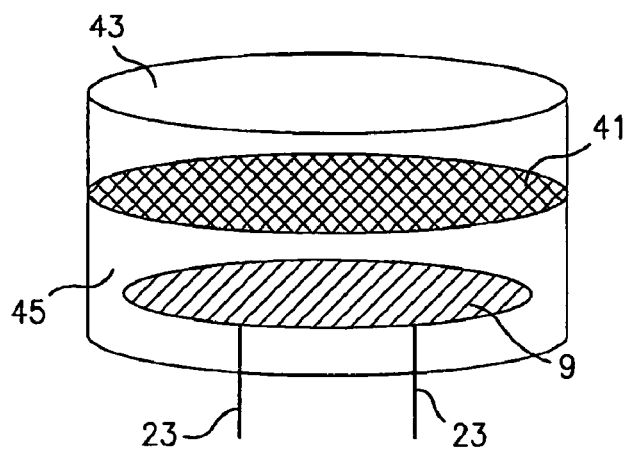
*FIG. 7*
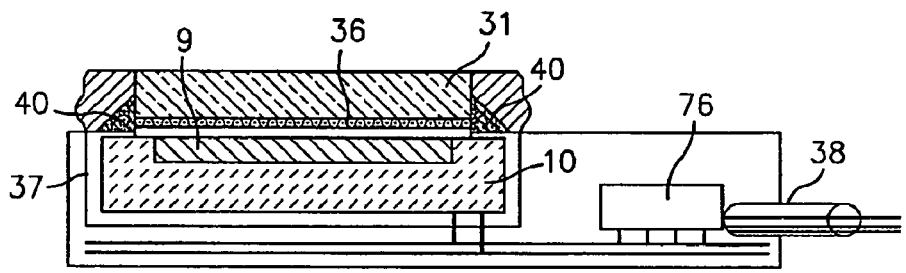
*FIG. 8*
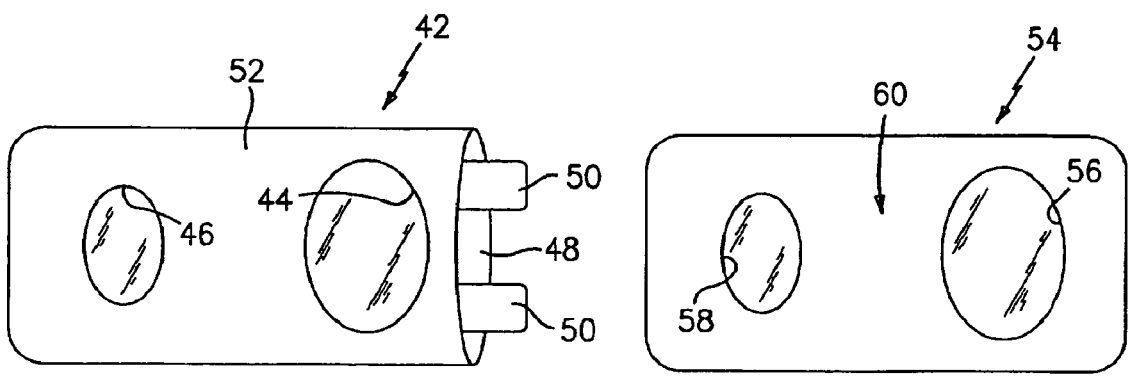
*FIG. 9*  *FIG. 10*

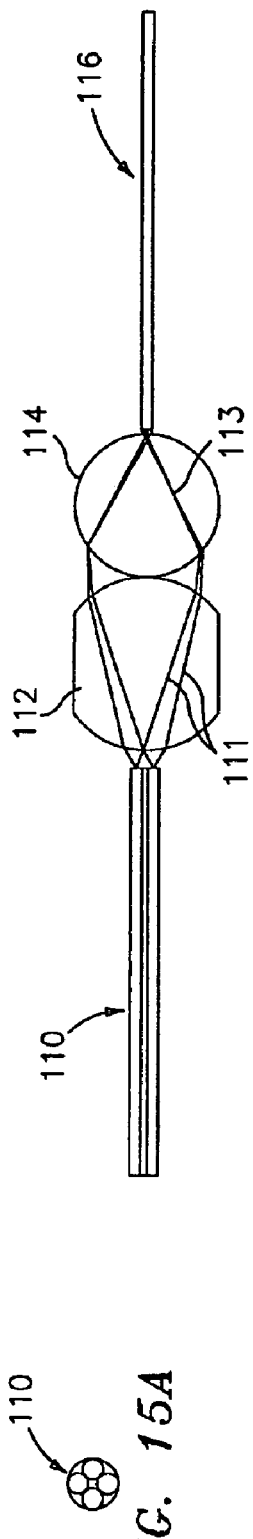
FIG. 15A
FIG. 15
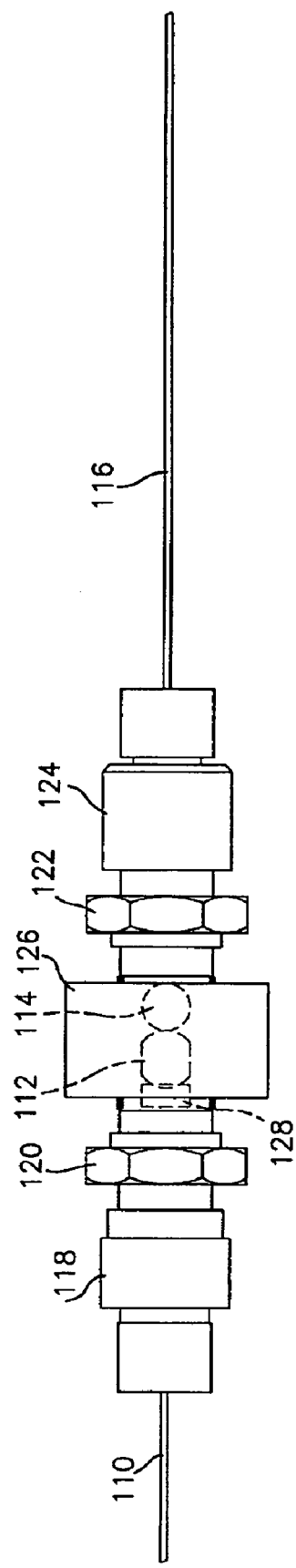
FIG. 16
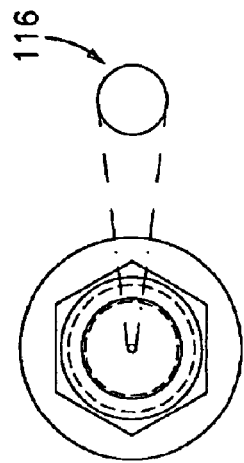
FIG. 16B
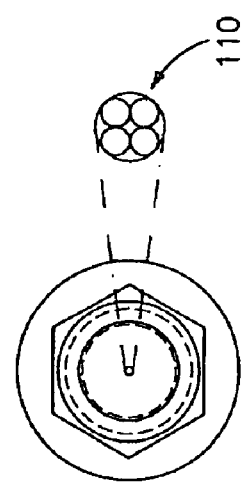
FIG. 16A

LASER DIODE OPTICAL TRANSDUCER ASSEMBLY FOR NON-INVASIVE SPECTROPHOTOMETRIC BLOOD OXYGENATION

This application is a continuation of U.S. patent application Ser. No. 09/951,221 filed Sep. 14, 2001, now U.S. Pat. No. 7,047,054, which is a continuation in part of U.S. patent application Ser. No. 09/434,142 filed Nov. 4, 1999, now abandoned, which claimed the benefit of the filing dates of U.S. Provisional Patent Application Nos. 60/123,849, filed Mar. 12, 1999; and 60/151,319 filed Aug. 30, 1999.

This invention was made with Government support under the terms of Contract No. 1R43NS39723-01 awarded by the Department of Health and Human Services. The Government has certain rights in the invention.

TECHNICAL FIELD

This invention relates to an improvement in a non-invasive near-infrared spectrophotometric (NIRS) optical transducer assembly, and a method of using the same. More particularly, this invention relates to a practical NIRS optical transducer assembly which can be reusable, is safe to use, and which can provide an accurately sized and consistent laser light field on a subject's skin.

BACKGROUND ART

Near-infrared spectroscopy (NIRS) is an optical spectrophotometric method of continually monitoring tissue oxygenation. The NIRS method is based on the principle that light in the near-infrared range (700 to 1,000 nm) can pass easily through skin, bone and other tissues but, within these wavelengths, hemoglobin has specific absorption spectra, dependent upon its oxidation state, i.e., oxygenated-hemoglobin ($HbO_2$); and deoxygenated-hemoglobin (Hb). By using light sources that transmit near-infrared light at specific different wavelengths, and measuring changes in transmitted or reflected light attenuation, oxygenation concentration changes of $HbO_2$ and Hb can be monitored.

Total hemoglobin is the summation of the two states of hemoglobin (Total Hb=$HbO_2$+Hb), and is proportional to relative blood volume changes, provided that the hematocrit or hemoglobin concentration of the blood is unchanged. The most valuable aspect of NIRS is that it allows one to continually monitor cerebral oxygenation levels in an adult or neonate, especially in diseased conditions, in which oxygenation levels in the brain can be compromised, leading to brain damage or death.

It is known that near-infrared light passes through the skin and the skull of a neonate readily, and is absorbed by certain biological molecules in the brain. Near-infrared spectroscopy (NIRS) detects oxygenation changes in biological tissue (brain, muscle, or other organs) mainly at the micro circulation level (capillaries, arterioles, and venuoles) based on different absorption characteristics of the chromophores oxyhemoglobin ($HbO_2$) and deoxyhemoglobin (Hb) in the near-infrared spectrum (700-1,000 nm). Average tissue penetration is 2-3 cm with sub-second time resolution.

Another spectrophotometric method, called pulse oximetry, determines arterial oxygen saturation ($SaO_2$) of peripheral tissue (i.e. finger, ear, nose) by monitoring pulsatile optical attenuation changes of detected light induced by pulsatile arterial blood volume changes in the arteriolar vascular system. The method of pulse oximetry requires pulsatile blood volume changes in order to make a measurement. Since venous blood is not pulsatile, pulse oximetry cannot provide any information about venous blood. Conversely, NIRS does not require pulsatile blood volume to calculate parameters of clinical value.

Relative changes of the concentrations of $HbO_2$ and Hb can be quantified by using the modified Beer-Lambert Law, which takes into account the optical attenuation in a highly scattering medium like biological tissue. The modified Beer-Lambert Law can be expressed as:

$$A=-\log(I/I_0)_L=(å_L \times C \times d \times B)+G \qquad \text{(Equation 1);}$$

wherein A is the optical attenuation in tissue at wavelength L (units: optical density OD); $I_0$ is the incident light intensity (units: $W/cm_2$); I is the detected light intensity; (L is the wavelength-dependent absorption coefficient of the chromophore (units: $OD \times cm^{-1} \times \mu M^{-1}$); C is the concentration of chromophore (units: $\mu M$); d is the light source-to-detector distance (units: cm); B is the light scattering differential path length factor (unitless); and G is a factor relating to tissue geometry and scattering of light (units: OD).

Absolute measurement of chromophore concentration is very difficult because G is unknown. However, over a reasonable measuring period of several hours to days, G remains constant, allowing for the measurement of relative changes of chromophore from a zero reference baseline. Thus, if time $t_2$ is an arbitrary time after the start of the optical measurement at $t_1$ (baseline), differential attenuation (A) can be calculated, canceling out the variables G and $I_0$, providing that they remain constant. The objective is to determine changes in chromophore concentration [$\Delta C=C(t_2)-C(t_1)$] from A derived from the equation:

$$\Delta A=-\log(I_2/I_1)_L=å_L=\Delta C \times d \times B \qquad \text{(Equation 2);}$$

NIRS algorithms that are designed to calculate the relative changes of more than one chromophore use the multivariate form of Equation 2. To distinguish between, and to compute relative changes in, oxyhemoglobin ($\Delta HbO_2$) and in deoxyhemoglobin ($\Delta Hb$), a minimum of two different wavelengths, preferably from narrow spectral bandwidth light sources, like laser diodes, are preferred. The units of $\Delta HbO_2$ and $\Delta Hb$ are in (moles per liter of tissue ($\mu M$) which is determined from a dimensional analysis of Equation 1.

It would be desirable to have a reusable NIRS transducer assembly having the ability to accurately control the energy level and size of a laser light field cast upon a subject's skin as well as improving the light detector signal-to-noise ratio by employing an improved EMI shielding scheme during use of the assembly. It would be desirable to combine light from multiple light sources into a single output fiber optic that is lightweight, and flexible, while providing sufficient light coupling efficiency. It would be desirable to have a transducer dislodgement-laser safety interlock system that would require no extra light source or detector components, while having the ability to disable laser operation due to transducer attachment failure and laser operation failure as well as a scheme that will verify secure transducer attachment before laser activation.

DISCLOSURE OF THE INVENTION

This invention relates to an improved transducer assembly for use in near-infrared spectroscopy (NIRS) of human patients. A prism providing a laser light source directing means, and one or more photodiodes are contained in a flexible housing which can be easily and securely attached to a subject's head, or some other part of the body. A rigid light guide placed over the prism provides a constant light intensity output of the spectrophotometric measuring system during a measuring period, by maintaining a constant laser light source to skin distance. A light detection means, by utilizing one or more photodiodes, allows for detection of laser light at a predetermined distance(s) away from the light source. The detection of light is improved by implementing an EMI shielding scheme that allows for attenuation of EMI interference while preserving an optical pathway for light to reach the detector via an EMI shielded optically transparent rigid window. An improved method of combining light from multiple light sources into a single output fiber optic that is lightweight, and flexible, while providing sufficient light coupling efficiency for a spectrophotometric measuring system is disclosed. An improved transducer dislodgement-laser safety interlock system is disclosed which does not require extra light source or detector components, while having the ability to disable laser operation due to transducer attachment failure and laser operation failure as well as verifying secure transducer attachment before laser activation.

The NIRS transducer assembly of this invention may consist of two separable components, the NIRS transducer housing containing the laser light source and photodiode(s) described above; and a disposable adhesive envelope or pad which is used to mount the NIRS transducer assembly housing easily and securely to the subject's skin. It is economically more feasible to use a non-disposable NIRS transducer housing with a disposable envelope rather than a disposable NIRS transducer housing, while maintaining all of the advantages of single use, disposable transducer applications, especially in a health care environment, in which sanitation and sterilization requirements are paramount.

The advantage of using a light radiation with a narrow spectral bandwidth (<1-3 nm) is maintained.

The rigid laser light guide, which is placed over the output window of the laser light redirecting prism, has several functions. One function is to further decrease the intensity of laser light on the skin of a subject undergoing spectrophotometric monitoring by taking advantage of the conical radiation characteristics of the laser diode coupled to a optical light guide such as a multimode or single mode fiber optic. Thus, with an increasing separation distance (r) between the laser diode fiber optic output and the skin surface, the intensity (power/area) of the laser light decreases by a factor of $r^2$. The prism, which redirects the laser-fiber optic output provides most of the separation distance from the light source to skin. The use of the laser light guide increases the separation distance and thus further decreases light intensity on the skin. This is important for designing a laser light source based optical transducer assembly meant to be directly applied to a human forehead, or some other part of the human body. To assure safety for the skin and tissue, the laser diode optical transducer assembly must be designed to operate within the limitations which are imposed by the "Maximum Permissible Exposure" (MPE) values set forth by the American National Standard for the safe use of lasers (ANZ136.1-1993).

The laser light guide is rigid and provides a planar interface between the assembly and the patients skin in which the laser light is illuminating. The light guide controls the spacing between the prism and the subject's skin, and therefore controls the incident light intensity $I_0$ (from Equation 1) on the subject's skin. This is especially important when attempting to measure absolute chromophore values as determined from Equation 1.

One or more photodiodes are also incorporated in the NIRS transducer assembly housing, separated from the laser diodes light source by from a few mm to more than about 60 mm, depending on the size of the subject being monitored. For a typical adult human head, it is believed that at least 45 mm separation distance is needed for adequate brain blood oxygenation monitoring, using a reflection mode type of the NIRS transducer assembly. Multiple photodiodes can be used to monitor different depths of blood oxygenation in the subject, or can be used as reference detectors for algorithms that compensate for the scalp component of the detected signals. For neonates, shorter separation distances between the laser diodes and the photodiodes of around 20 mm can be used for reflection mode monitoring, or large distances over 60 mm can be used for trans-cranial mode NIRS transducer assembly. Photodiodes with larger surface areas can be used as the laser light source-to-photodiode separation distances increase to compensate for the decreasing light levels detected from larger separation distances or lower power light sources.

A photodiode preamplifier, placed next to the photodiode, or farther away as a separate assembly, allows for amplification of the detected low light level signal, and then provides the amplified signal to the NIRS system processor.

A partially optically transparent, and electrically conductive shield which surrounds the photodiode can be used to attenuate ambient electromagnetic interference (EMI) noise which is otherwise transmitted to the photodiode. A window in the shield exposes the photodiode's photosensitive surface to detected light from the laser diodes. The optically transparent electrically conductive shield may include a thin metal wire screen, an electrically conductive transparent coating, or the like. By placing an optically transparent rigid spacer over the photodiode light sensitive surface, further EMI attenuation can be achieved by reducing the capacitive coupling between the subject's skin and the photodiode photosensitive surface.

The use of a disposable adhesive envelope or pad for the purpose of securing the NIRS transducer assembly housing to the subject's skin renders the transducer assembly housing reusable from subject to subject. The disposable adhesive envelope or pad can be pre-sterilized thereby providing additional protection to the subject. The disposable envelope or pad will also protect the NIRS transducer assembly housing from any residue from the subject, allowing the NIRS probe housing surface to remain uncontaminated, thus making it safer and easier to reuse.

Different NIRS transducer assemblies are designed to be interchangeable with different NIRS system processors/monitors by incorporation of custom laser diode drivers and encoded calibration parameters in a connector housing. The NIRS system processor has an interface port for the connector housing. The connector housing may contain customized laser diode automatic power control (APC) drivers, which are individually adjusted to provide a predetermined laser diode output power. By providing encoded calibration parameters in the connector housing, the NIRS system processor can determine the characteristics of each individual NIRS transducer and laser diode characteristics by a decoding mechanism, calibrating the NIRS algorithm to provide accurate computation with different transducer assemblies and individual laser diode characteristics.

To minimize complexity of the NIRS transducer assembly, a single core multimode fiber optic is used as a light guide to transfer laser light from a detachable connector to the prism inside the transducer housing. A multi-fiber optic combiner assembly channels light from multiple laser light sources into a single fiber optic by utilizing two ball lenses of predetermined characteristics. The advantage of using a ball lens multi-fiber optic combiner is that a smaller diameter single core multimode output fiber optic can be used. Use of a smaller core fiber optic in the cable interfacing the NIRS transducer housing to the detachable connector, reduces weight, increases flexibility, and reduces induced torque from bending.

The incorporation of several laser safety interlock schemes further minimizes the possibility of unnecessary laser light exposure to personnel using the optical transducer. The safety interlock system inhibits laser diode pulsing immediately if the optical transducer is not securely attached to the subject. The three interlock schemes include: 1) monitoring ambient light conditions; 2) monitoring laser output range; and 3) monitoring sudden changes in detected laser output over a period of time.

When the optical transducer is attached properly to the subject's forehead in normal daytime operation, the detected ambient light level is low because the probe body shields outside light. When the detected ambient light reaches a predetermined level, indicating possible transducer detachment or improper placement, laser operation is inhibited. Accidental probe detachment will automatically shut down the laser diodes.

For night-time operation of the NIRS system, additional interlock systems are employed. The light detector in the optical transducer continuously monitors the laser diode output. If the detected laser signal falls out of a predetermined range, then immediate laser shutdown occurs. Also, if the detected laser signal suddenly changes a predetermined amount over a predetermined time period due to probe disruption or detachment, immediate laser shutdown will occur. Any event that indicates probe detachment will require user intervention to re-attach the probe and to reset the NIRS system laser safety interlock before laser diode pulsing can resume.

Enabling but non-essential details of the invention will become more readily apparent from the following detailed description of the invention when taken in conjunction with the accompanying drawings in which:

BRIEF DESCRIPTION OF THE DRAWINGS

FIG. 7 is an enlarged sectional view of an alternative photodiode packaging showing details of the EMI shielding mechanisms;

FIG. 8 is an enlarged sectional view of the photodiode with preamplifier amplifier showing details of the EMI shielding mechanisms employed;

FIG. 9 is a plan view of a disposable self-adhesive envelope which is designed for use in containing the transducer assembly housing of FIG. 1;

FIG. 10 is a plan view of a disposable self-adhesive pad which is designed for use in connection with the transducer assembly housing of FIG. 1;

FIG. 15 is a light ray diagram of the multi-fiber optic light combiner assembly;

FIG. 16 shows the details of the multi-fiber optic light combiner assembly;

DETAILED DESCRIPTION THE INVENTION

Figure 1:
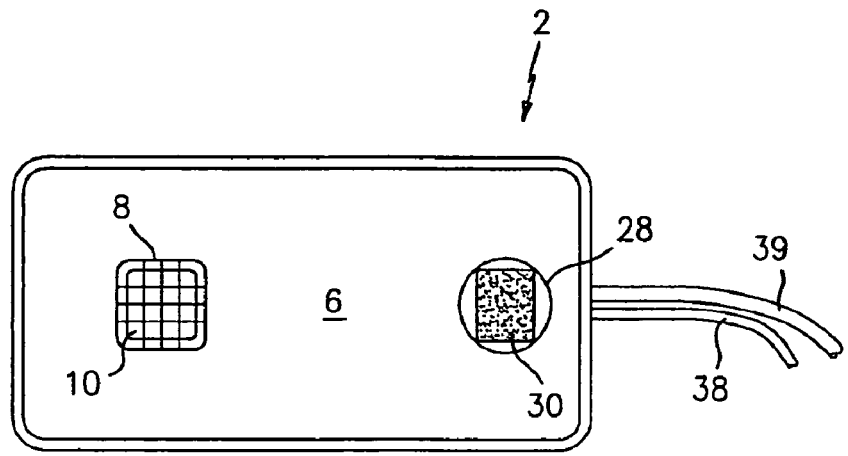
FIG. 1 is a plan view of one embodiment of a reflective NIRS transducer assembly which is formed in accordance with this invention.
Figure 2:
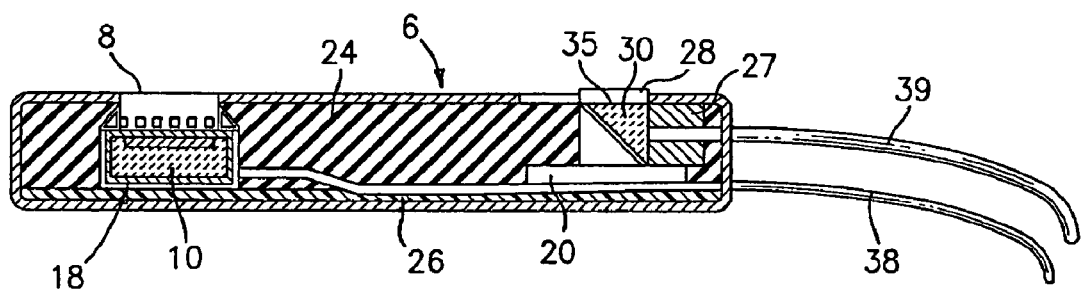
FIG. 2 is a side sectional view of the transducer assembly of FIG. 1.

Referring now to the drawings, there is shown in FIGS. 1 and 2 an embodiment of a reflective-type NIRS transducer assembly which is denoted generally by the numeral 2. The transducer assembly 2 includes a housing 4 which contains the components of the transducer assembly 2. The housing 4 includes a flexible light-shielding surface rubber layer 6 having a first window 8 allowing light to reach the EMI shielded photodiode assembly 18 which is disposed in the housing 4. The surface layer 6 is made of a durable material to allow attachment and removal of a disposal adhesive attachment method. A laser light guide 28 is overlying and optically coupled to the prism 30, which protrudes slightly from surface layer 6. The sides of photodiode window 8 and light guide 28 perpendicular to surface layer 6 are painted with a light-shielding material to prevent optical shunting, i.e., light from entering through the sides of the windows. In an alternative embodiment, the surface of window 8 and light guide 28 are flush with the exposed surface of surface layer 6. Fiber optics 39 direct light from remotely located laser diodes to the prism 30 and are secured in place by the fiber optic mount 27. The housing 4 also includes a flexible, electrically and optically insulating body 24 which can be formed from rubber or some other suitable elastomer, attached to a flexible support structure 26. The light source assembly 20, the EMI-shielded photodiode assembly 18, and surface layer 6 are also mounted on the flexible support structure 26. Another shielded cable 38 interconnects the photodiode assembly 18 and the NIRS system processor assembly via an interface connector housing (See FIG. 13). The NIRS system processor analyzes the results of the NIRS reflectance data gathered by the photodiode 10.

Figure 3:
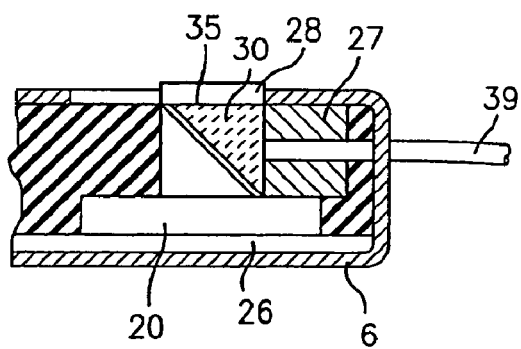
FIG. 3 is a view of the light source portion of the embodiment of FIG. 2.

Referring now to FIG. 3, details of the light source assembly 20 is shown. The light redirecting prism 30 is connected to the rigid light guide 28 which provides surface-to-surface contact between the prism 30 and the subject's skin S. The light guide 28 is rigid so that when it is pressed against the subject's skin during the monitoring of blood oxygen, the surface S of the skin is flattened, and the distance between the fiber optic 39 output and the skin surface S via the prism 30 is constant across the entire illuminated area of the skin.

Figure 4:
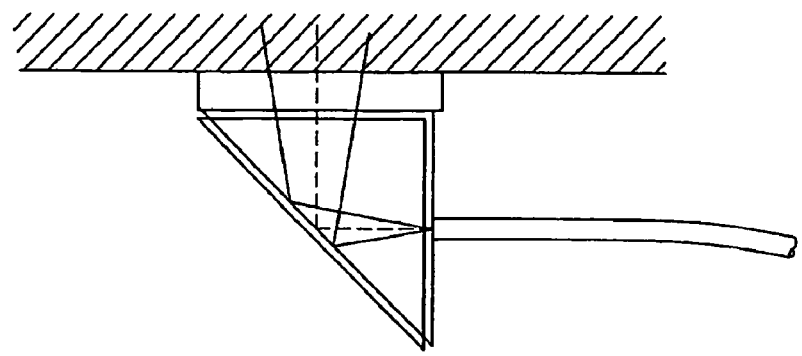
FIG. 4 is an enlarged sectional view showing the relationship between the transducer assembly fiber optic laser light source, prism, and rigid light guide with the subject's skin.

Shown in FIG. 4 are the arrangements of the light guide 28 and prism 30 demonstrating how the distance "r" between the laser coupled fiber optic 39 output and the surface S of the subject's skin can be controlled. First of all, it is noted that the planar surface S' of the light guide 28, when pressed against the subject's skin S, will flatten the contacted area of the subject's skin S so that the distance "r" between the laser coupled fiber optic 39 and the subject's skin S is constant for the entire skin area which is illuminated by the light guide 28. The inclusion of the light guide 28 with the prism 30 results in the effective length of "r" since $r=r_1+r_2+r_3$. Thus, with the light guide plus prism arrangement, one can effectively reduce the light intensity of the laser coupled fiber optic 39 output field which is delivered to the subject's skin S. If further attenuation means of the laser light field imposed on the skin S' is desired, then the light guide 28 may include a selective filter 29. The selective filter 29 may consist of a light-attenuating neutral density filtering element, or a light-diffusive element, such as a milky white semi-transparent plastic material, or both, in combination.

Figure 5:
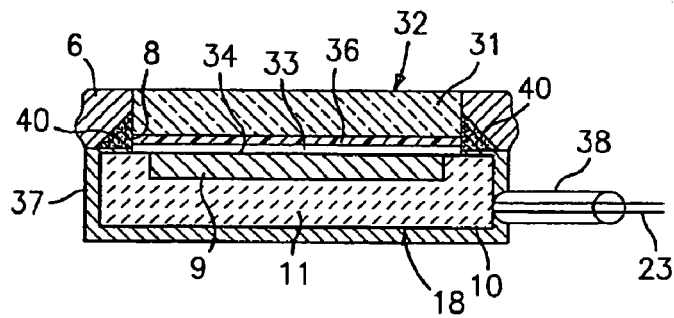
FIG. 5 is an enlarged sectional view of the photodiode portion of the transducer assembly of FIG. 2 showing details of the wire mesh type EMI shielding mechanisms for the photodiodes.
Figure 5A:
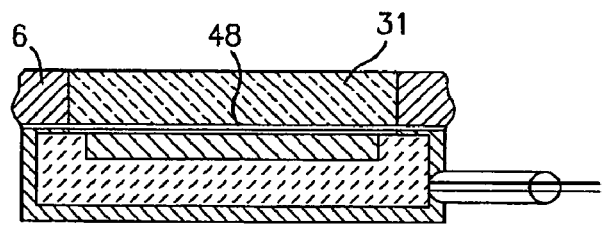
FIG. 5A is an enlarged sectional view of the photodiode portion of the transducer assembly of FIG. 2 showing details of the electrically conductive thin film type EMI shielding mechanisms for the photodiodes.
Figure 6:
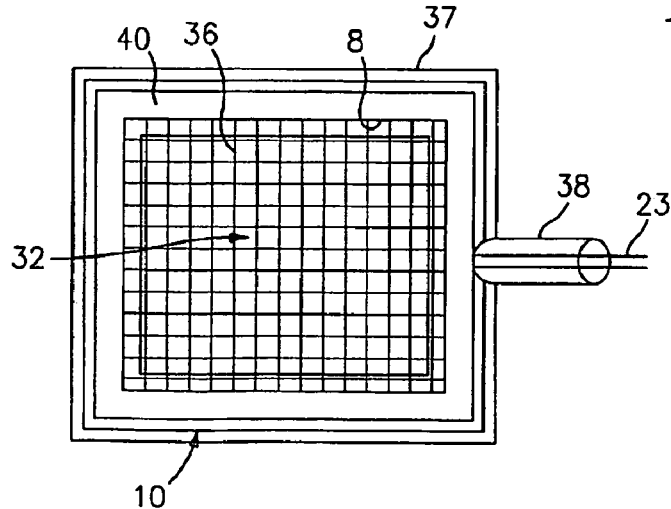
FIG. 6 is an enlarged plan view of the EMI shielded photodiode portion of the transducer assembly of FIG. 2.

FIGS. 5, 5A, and 6 illustrate an ambient EMI shielding arrangement for the photodiode detector window 8. An EMI shielded and optically transparent pane 32 of predetermined thickness, is positioned over the light sensitive surface 34 of the photodiode detector 10. The photodiode detector 10 includes a light-sensitive element 9 which is disposed in a ceramic cup 11. A wire mesh 36 is embedded between two optically transparent members 31 and 33, which form the pane 32. The mesh 36 will allow at least about 60% optical transmission of the reflected light from the laser light source 20 after passage through biological tissue to reach the photodiode 10. A non-porous EMI shield 37, such as an electro-conductive metal foil, surrounds the non-light sensitive parts of the housing, including the photodiode lead 23. An electrically conductive gasket 40, such as silicone paste, adhesive, foam, or other similar material, is used to create an electrical interface between the wire mesh 36 of the EMI shielded pane 32 and the non-porous EMI shield 37.

In an alternative EMI shielding embodiment, the wire mesh 36 could be placed directly over the photodiode light sensitive surface 34, and an optically transparent, electrically insulating pane 32 having a predetermined thickness, formed from a material such as glass, could then be placed over the wire mesh 36.

FIG. 5A shows an alternative embodiment in which the wire mesh 36 and lower optical member 33 are replaced with a thin optical member 48 that is coated with an electrically conductive, optically transparent thin film on one side. The electrically conductive film of thin optical member 48 is electrically interfaced to the non-porous EMI shield 37 by electrically conductive epoxy, adhesive, paste, or the like. In an alternative embodiment, the optical member 31 may be coated with an electrically conductive, optically transparent thin film on the side facing the photodiode 10.

FIG. 7 shows how a photodiode packaged in the "can" style package 45 can be EMI shielded by applying a wire mesh or thin film EMI shield 41 over the photodiode package "can" aperture. An electrically insulating, optically transparent window 43 would then cover the EMI shield 41.

FIG. 8 shows a preamplifier 76 placed next to photodiode 10, and enclosed in the EMI shielding structures similar to those described in FIG. 5 through FIG. 7.

These shielding structures reduce undesirable EMI generated noise, and improve the signal to noise ratio of the photodiode by two different methods. The wire mesh 36 or electrically conductive film 48 in combination with the non-porous electro-conductive material 37 creates a Faraday Cage around the photodiode 10, while allowing light to reach the photodiode 10 light-sensitive surface 34. By using an EMI attenuating optically transparent pane 32 of a predetermined thickness, preferably of about 1 mm or greater, further EMI attenuation is attained by increasing the photodiode-to-biological tissue separation distance. This optically transparent spacer reduces the capacitance between the photodiode light sensitive surface 34 and the biological tissue, such as human skin, resulting in the increased reduction in electromagnetic coupling and generated noise currents when compared to using the Faraday Cage shielding method without the optical spacer.

To construct the EMI shielded optical sensor, commercially available EMI shielded wire mesh windows from Chomerics (Woburn, Mass.) can be used. Chomerics "EMI CLARE"™ GP 70 EMI shielded windows provide 60 to 70% light transmission, with different pane thicknesses of 1.66 mm; 2.00 mm; and 3.00 mm being available. The transparent panes 32 and the mesh 36 need to be sized to close the window 8 and cover the light-sensitive surface 34 of the photodiode 10, which surface 34 can range in size from four square mm to one hundred square mm. Alternatively, Chomerics "WIN-SHIELD"™ AgF8 conductive film can be used in place of the wire mesh window. This conductive film is 0.2 mm thick and has similar optical properties as the mesh window. In another embodiment, a copper mesh wire cloth like material from Sefar America, Inc. (Briarcliff Manor, N.Y.) can be used as an EMI shield over the photodiode photosensitive surface.

Referring now to FIGS. 9 and 10, there are shown two different types of discardable or disposable adjunct adherence devices that can be used in conjunction with the transducer assembly 2. FIG. 9 shows an envelope 42 which can be used to house the assembly 2. The envelope 42 has two transparent plastic windows or open apertures 44 and 46 which are sized and positioned to be in registry with light source assembly 20, and with the photodiode assembly 18, respectively. The transducer assembly 2 is inserted into the envelope 42 through an opening 48. The transparent window version of envelope 42 is used if the rigid laser light guide 28 and photodiode window 32 are flush with upper surface layer 6. The open aperture window version of envelope 42 is used if the rigid laser light guide 28 and photodiode window 32 protrude slightly from the upper surface layer 6 as shown in FIG. 1, with the respected windows locking into place. The envelope 42 also includes several clasps 50 that are used to secure the assembly 2 in place in the envelope 42. The surface 52 of the envelope 42 is formed from, or coated with, an adhesive material. The envelope 42 is preferably formed from a light-impermeable material such as rubber or black plastic. This prevents light from directly traveling between the laser diodes and the photodiode (i.e., no optical shunting) which could occur with a transparent envelope.

FIG. 10 shows a disposable or discardable adhesive pad 54 which can be releasably adhered to the transducer assembly 2 and to the subject's skin. The pad 54 is preferably formed from rubber or black plastic, and includes opposed adherent surfaces such as 60 which enable the pad 54 to be adhered to the transducer assembly 2 and to the subject's skin S. The pad 54 has two transparent plastic windows or open apertures 56 and 58 which are sized and positioned to be in registry with the light source assembly 20, and with the EMI shielded photodiode assembly 18, respectively. The transparent window version of pad 54 is used if the rigid laser light guide 28 and photodiode window 32 are flush with upper surface layer 6. The open aperture window version of pad 54 is used if the rigid laser light guide 28 and photodiode window 32 protrude slightly from the upper surface layer 6 as shown in FIG. 1, with the respective windows fitting through their respective open apertures. The envelope 42 and the pad 54 are both sterile prior to use, and can be discarded after being removed from the patient.

Figure 11:
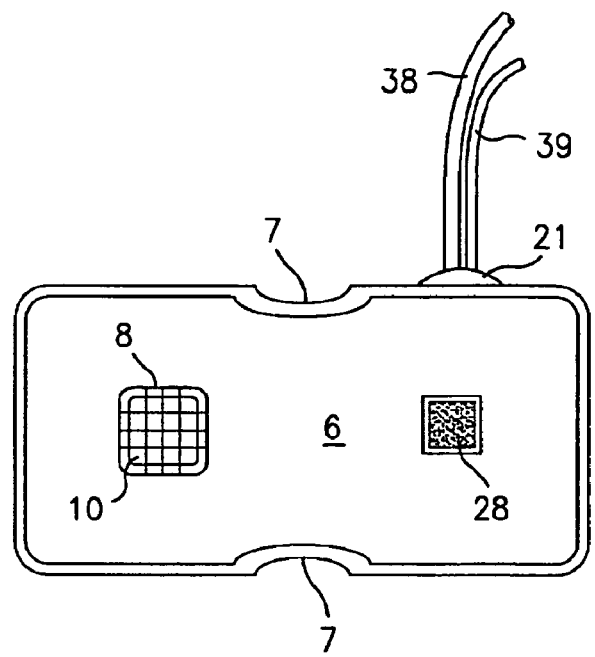
FIG. 11 is a plan view of another embodiment of a reflective NIRS transducer, in which the fiber optic and shielded cable leads exit at an angle of 90° from the configuration shown in FIG. 1 to form an "L"-shaped housing.
Figure 11A:
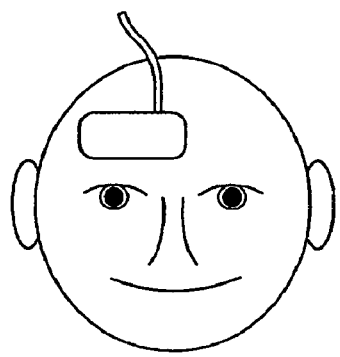
FIG. 11A shows how the "L"-shaped NIRS transducer of FIG. 11 is attached to a neonate's head.

FIG. 11 shows an alternative embodiment of the NIRS transducer assembly of FIG. 1 in which the fiber optic light guide 39 and shielded cable 38 exit the transducer housing 4 on the side, giving the probe assembly an "L" shape. A support appendage 21 further secures the fiber optics 39 and cable 38 to the transducer housing 4. Recessed cutouts 7 in the housing 4 as shown allow for added flexibility of the optical transducer 2 when applied to curved surfaces such as the -head or body appendage. This "L"-shaped NIRS optical transducer is especially useful for brain oxygenation monitoring on awake neonates and awake adults by allowing the fiber optics 39 and cable 38 to come off the subject over the crown of the head (see FIG. 11A) as opposed to the side of the subject's head when the transducer assembly is placed on the forehead. The fiber optics 39 and cable 38 are out of grasping range of a neonate's hand, reducing possible transducer disturbance. Also, the transducer is less likely to be disturbed when the neonate sleeps on his or her side, which may result in the neonate sleeping on the NIRS transducer fiber optic-shielded cable leads.

Figure 12:
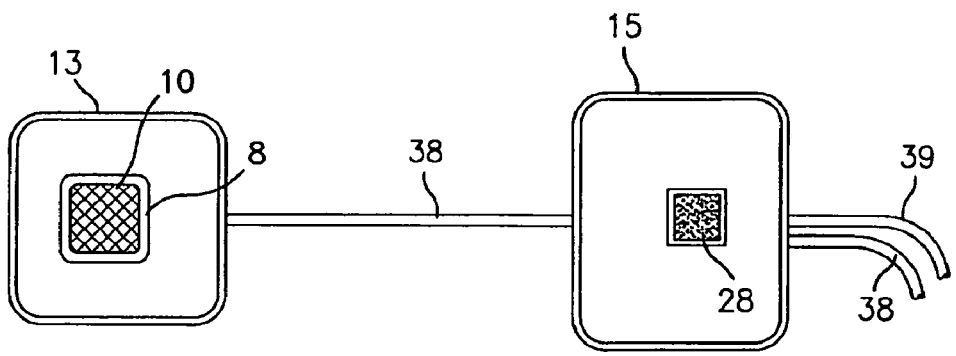
FIG. 12 is a plan view of another embodiment of a transmissive NIRS transducer assembly which is formed in accordance with this invention.

FIG. 12 shows an embodiment of a NIRS transducer assembly formed in accordance with this invention which is suitable for use with neonates. In this embodiment, the EMI shielded photodiode assembly 18 is contained on one shielded pod 13, and the light source assembly 20 is contained in another pod 15. The pods 13 and 15 are connected by the cable 38, and the fiber optic cable 39 extends from the pod 15 to the controller. The length of the cable 38 is sufficient to allow the pods 13 and 15 to be attached to opposite sides of the neonate's head to allow the monitoring of cerebral blood oxygenation.

Figure 13:
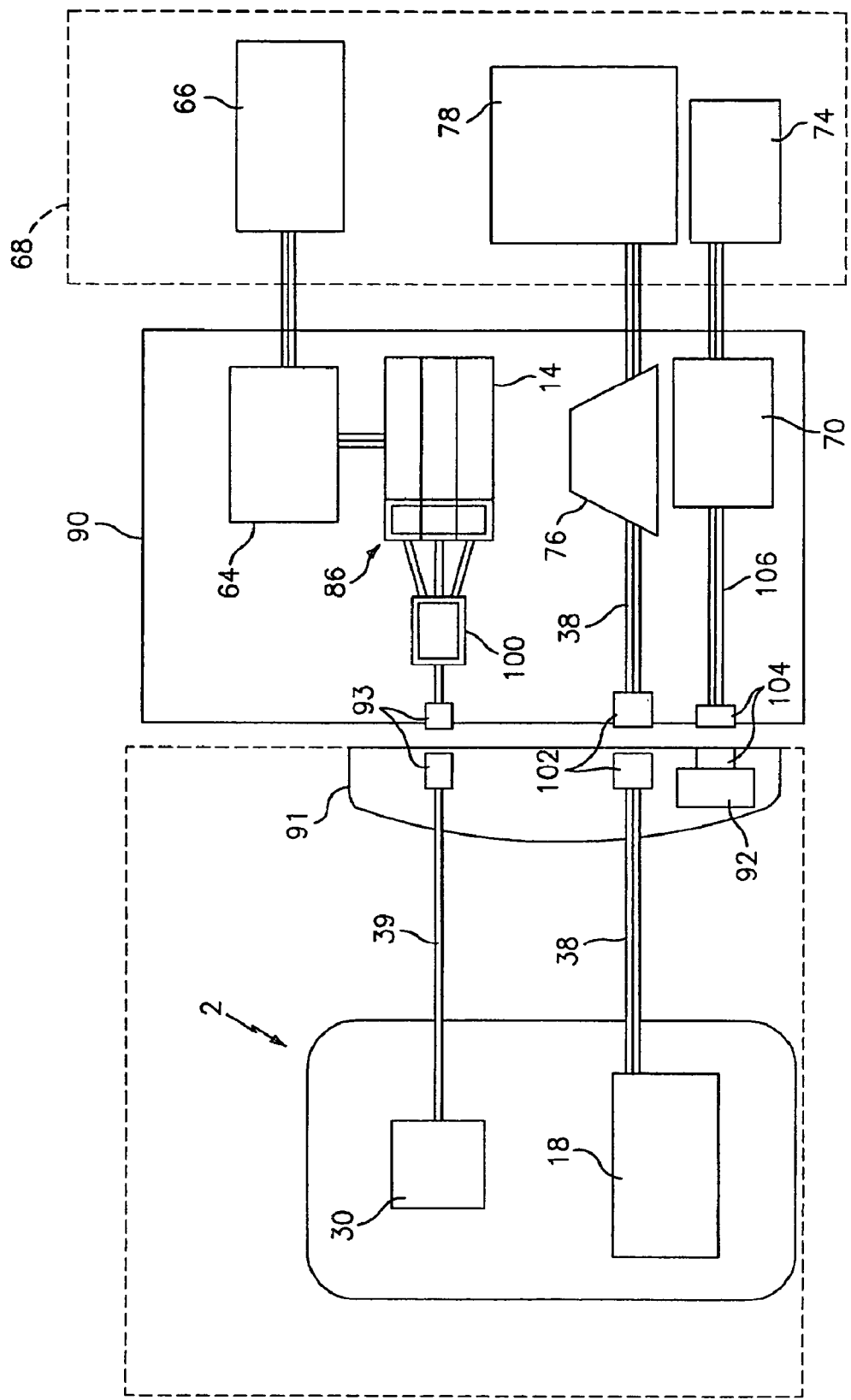
FIG. 13 is a schematic view of a NIRS transducer assembly formed in accordance with this invention which is associated with a connector housing, laser box assembly, encoding and decoding means of calibration parameters, and a NIRS system processor.

FIG. 13 illustrates the components of a NIRS transducer assembly connector housing 62 which enables interchangeability of the laser diodes and other components. The laser box housing 90 contains laser diode automatic power control drivers 64 which interface with the laser diodes 14. A laser diode sequencer control 66 forms a portion of the NIRS system processor 68 and provides multiplexed pulsing of the laser diodes 14. Each laser diode power output is adjusted by its respective automatic power control driver. There are three different laser diode pin-out configurations available, each of which requires different types of automatic power control drivers. Thus, incorporation of the automatic power control drivers 64 in the laser box housing 90 provides flexibility in the selection of the laser diodes 14.

The laser box housing 90 also contains a calibration parameter encoding mechanism 70, along with NIRS transducer encoded parameter mechanism 92, which provides the NIRS system processor with necessary information relating the laser box housing and NIRS transducer assembly characteristics. The calibration parameters include: laser diode wavelength; coefficients relating to the change in laser diode wavelength over temperature changes; laser diode automatic power control feedback monitor current and corresponding laser power output; transducer light source to photodiode separation distance; encoding coefficients indicating the type of NIRS transducer specifically intended to be used on a certain type of biological tissue, subject body part, or certain subject species; and other information as needed about the characteristics of the individual NIRS transducer assembly being employed. The calibration parameters may be encoded by the use of resistors of predetermined values, programmable read only memory devices, bar codes, or other suitable encoding instrumentalities. The encoded information is transmitted to a decoder 74 in the system processor 68.

The NIRS assembly detachable connector 91 allows for attachment and removal from the laser box housing 90. A fiber optic coupler 93 provides an interface for the single core fiber optic 39 of the NIRS transducer assembly and laser box 90. Similarly, the shielded cable coupler provides an interface for the photodiode output to the laser box and a second cable coupler 104 provides an interface to the transducer encoded parameters 92.

Figure 14:
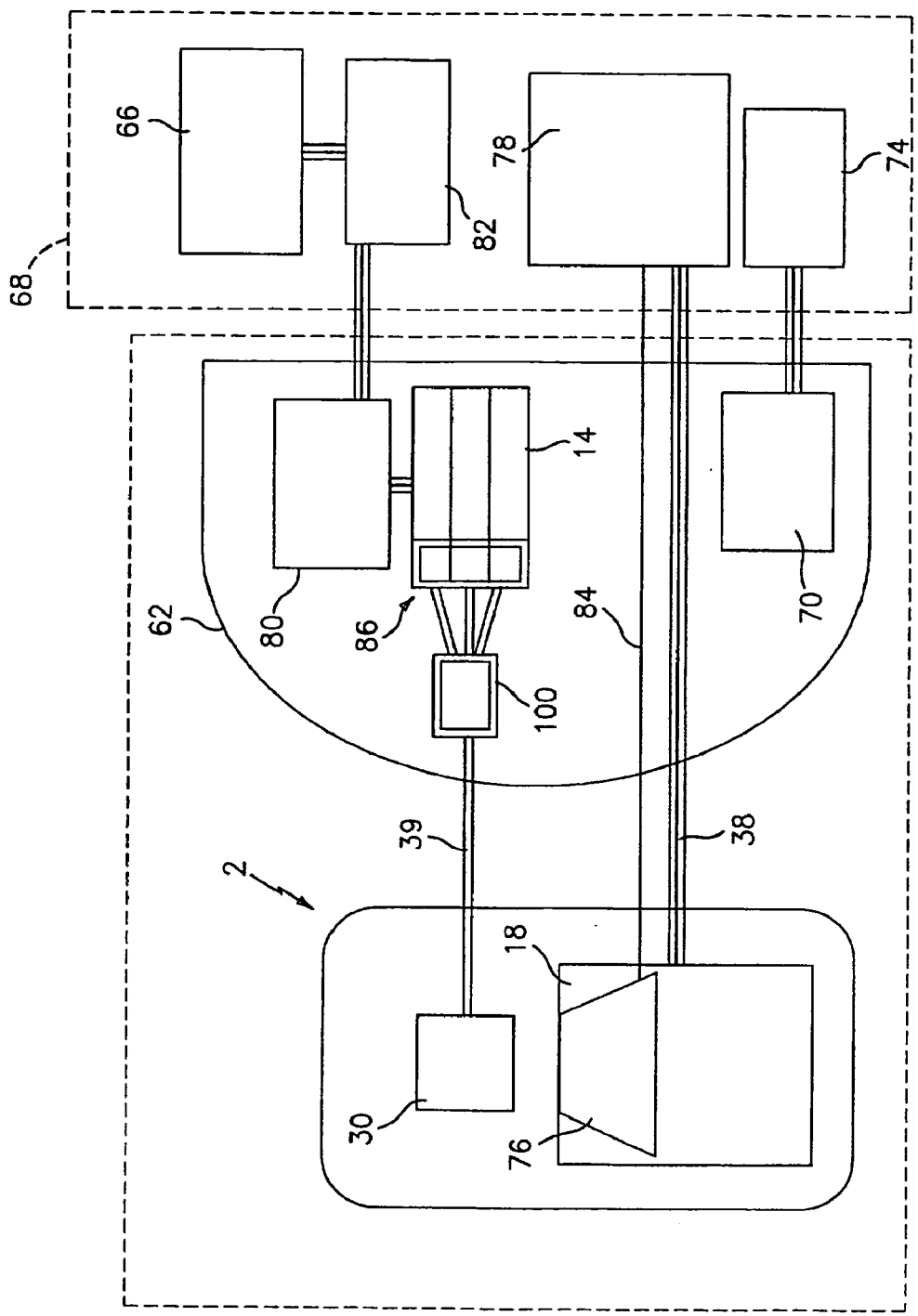
FIG. 14 is schematic view of a NIRS transducer assembly which is similar to FIG. 13, but showing partitioned laser power control drivers and the pre-amp portion of the system located in the assembly housing.

In an alternative connector assembly embodiment shown in FIG. 14, the automatic power control drivers 64 may be separated into adjustable components 80, and non adjustable components 82. In this embodiment, the adjustable components 80 are disposed in the connector housing 62 and the non-adjustable components 82 are incorporated into the NIRS system processor 68. The adjustable components 80 include variable potentiometers, which are used in adjusting the laser power output. The non-adjustable components 82 consist of fixed semiconductor and discrete electronic components, and are typically resistors and capacitors. The connector housing 62 also contains a calibration parameter encoding mechanism 70 which provides the NIRS system processor with necessary information relating the NIRS transducer assembly characteristics, as described previously.

A photodiode preamplifier 76 may be located in the connector housing 62 as shown in FIG. 13 for providing amplification of the light level signal from the EMI-shielded laser diode assembly 14 and transmitting the amplified signal to a signal processing and laser safety interlock control portion 78 of the NIRS system processor 68. FIG. 14 shows an alternative placement of the preamplifier 76, which can be integrated with, or placed next to, the photodiode 18 inside the transducer assembly 2. A preamplifier power cable 84 supplies power to the preamplifier 76.

The multi-fiber optic combiner assembly 100 shown in FIG. 13 and FIG. 14 allows for multiple laser light sources of different wavelengths to be coupled into a small diameter core fiber optic output 39 leading to transducer housing 2. The multi-fiber optic combiner assembly 100 is expanded in FIGS. 15-17 to show more detail. FIG. 15 shows the basic principle of using two ball lenses to focus light from the larger diameter fiber optic bundle 110 into a smaller diameter single core multimode fiber optic 116. Ball lens 112 refracts and collimates light from input fiber bundle 110, as shown by light rays 111. Ball lens 114 focuses the collimated light at, or just outside of, its surface into a small spot onto output fiber 116, as shown by light rays 113. Ball lens 114 has a higher refractive index "n" than ball lens 112 so as to focus the light onto a smaller diameter output fiber. Ball lens 114 may also have a smaller spherical diameter to further refract the light to a smaller spot size. The numerical aperture "NA" of the output fiber 116 is greater than or equal to the input fiber bundle 110, so as to allow maximum coupling of light to the output fiber 116.

Figure 17:
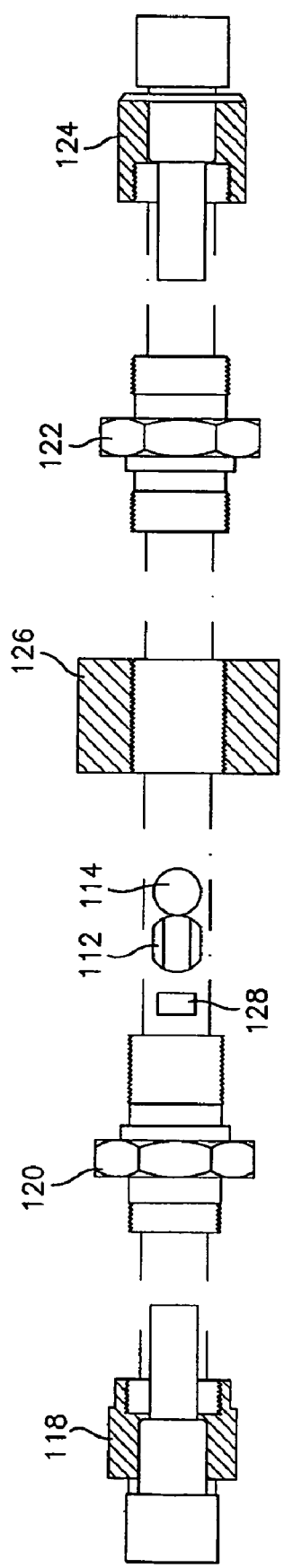
FIG. 17 shows details of the assembly process of the multi-fiber optic light combiner.

FIGS. 16 and 17 show a representative example of a multi-fiber optic combiner assembly 100. Four individual multimode fiber optics (0.39 NA, 200 gm core diameter, from 3M Company, St. Paul, Minn.) coupled to four different wavelength laser diodes are bundled together to form an input fiber bundle 110 with an outside diameter of 555 µm. Output fiber 116 is preferably a single multimode fiber optic with a core diameter of 300 µm and an overall core/cladding diameter of 325 µm (0.39 NA, from 3M Company, St. Paul, Minn.). The ball lens 112 can be made of BK7 glass which has a refractive index (n) of 1.52. The spherical diameter of the ball lens 112 is preferably 4 mm, which is trimmed into a drum shape with a diameter on one axis of 3.2 mm. The ball lens 114 preferably has a spherical diameter of 3.2 and is preferably made of sapphire which has a refractive index (n) of 1.77. The laser pigtailed input fiber light coupling efficiency into the output fiber with the ball lens arrangement is about 55 to 60%. Using anti reflective coatings on the ball lenses can further improve the coupling efficiency.

The input fiber bundle 110 terminates in a SMA 905 type fiber optic connector 118 and the output fiber optic 116 terminates in a second SMA connector 124. To assemble together, connector 124 is inserted into SMA coupler assembly consisting of coupler components 120, 122, and 126. The ball lenses, having an outside diameter of 3.2 mm slide snugly into the 3.2 mm inside diameter of the SMA coupler assembly, centering the ball lenses to the fiber optic center axis. A hollow spacer 128 is inserted next to ball lens 112 to focus the input fiber bundle 110 light onto output fiber 116. Alternatively, an adhesive can be used to secure the ball lenses into position. In an alternative embodiment, a spacer 128 can be inserted between the ball lens 114 and the output connector 124 for focusing purposes. Finally, an input connector 118 is inserted snugly into the SMA coupler assembly. The advantages of this assembly are that standard components are used, with automatic ball lens centering on the fiber optic light transmission axis, and one-step alignment with the spacer 128.

The NIRS transducer assembly 2 of this invention operates as follows. The assembly 2 has a multiplexed laser diode firing system in which only one laser diode at a time (emitting one wavelength) is pulsed "ON" and is modulated at a predetermined carrier frequency. The automatic power control (APC) drivers 64 for the laser diodes 14 will also operate at the predetermined modulation rate while maintaining the tight power tolerance. There is a dark period in which all of the laser diodes 14 will be "OFF", allowing for offset voltages to be sampled and subtracted. The duration of the dark period is usually much longer than the time period when the laser diodes are "ON". Thus, the overall duty cycle of the laser diodes is small. The photodiode located in the NIRS probe detects the laser light that irradiates the biological tissue. A transimpedance photodiode preamplifier converts the detected light to a voltage. A band pass filter of predetermined bandwidth, centered on the carrier frequency will be the first step in filtering out noise from the detected signal. Demodulation of the detected signal further attenuates noise and removes the carrier frequency. An adjustable gain amplifier will be used to increase the detected light levels to the desired range. An analog-to-digital converter demultiplexes each wavelength, the converter being controlled by timing circuitry that is synchronized with the laser diode pulsing. The data obtained is processed by a computer by use of a multivariate Modified Beer-Lambert Law algorithm which calculates the physiological parameters of interest. The determined physiological parameters: (Hb), (HbO$_2$), and (Total Hb) are displayed on a monitor.

The NIRS algorithm employed by the assembly of this invention is based on a multivariate form of the Beer-Lambert Law which is expressed in a matrix form since three laser diodes are employed. Relative changes of the concentrations of HbO$_2$ and Hb can be quantified by using the modified Beer-Lambert Law, which takes into account the optical attenuation in a highly scattering medium like biological tissue. Absolute measurement of chromophore concentration is very challenging because the determination of optical attenuation due to scattering losses is difficult. However, by measuring differential optical attenuation from an initial baseline, optical attenuation due to scattering is canceled out. The multivariate form of the modified Beer-Lambert Law requires that optical attenuation needs to be measured at least two different wavelengths to determine the two unknown chromophores (HbO$_2$ and Hb). If the number of wavelengths used is equal to the number of chromophores of interest, then the solution can be solved by Cramer's Rule. If the number of wavelengths used is greater than the number of chromophores of interest, as in the case of the NIRS system described above, a least squares multi linear regression method is used in the algorithm to solve for the chromophores of interest. In theory, the greater the number of measurement wavelengths the more increased reduction of errors in the determination of the chromophore concentration is achieved. Thus, the use of three laser diodes to measure two chromophores, as described above, will result in a more accurate measurement of the two chromophores. It will be appreciated that the system described above could also be modified to measure a third chromophore in biological tissue, such as cytochrome.

The laser intensity utilized will be far below the threshold indicated in ANSIZ 136.1-1993 for cases of accidental eye exposure. This is because of the conical radiation pattern, low duty cycle, and the low power level of the laser light. The incorporation of a laser safety interlock further minimizes the possibility of laser light exposure to personnel using the NIRS system. The safety interlock system inhibits laser diode pulsing immediately if the NIRS assembly is not securely attached to the subject.

Figure 18:
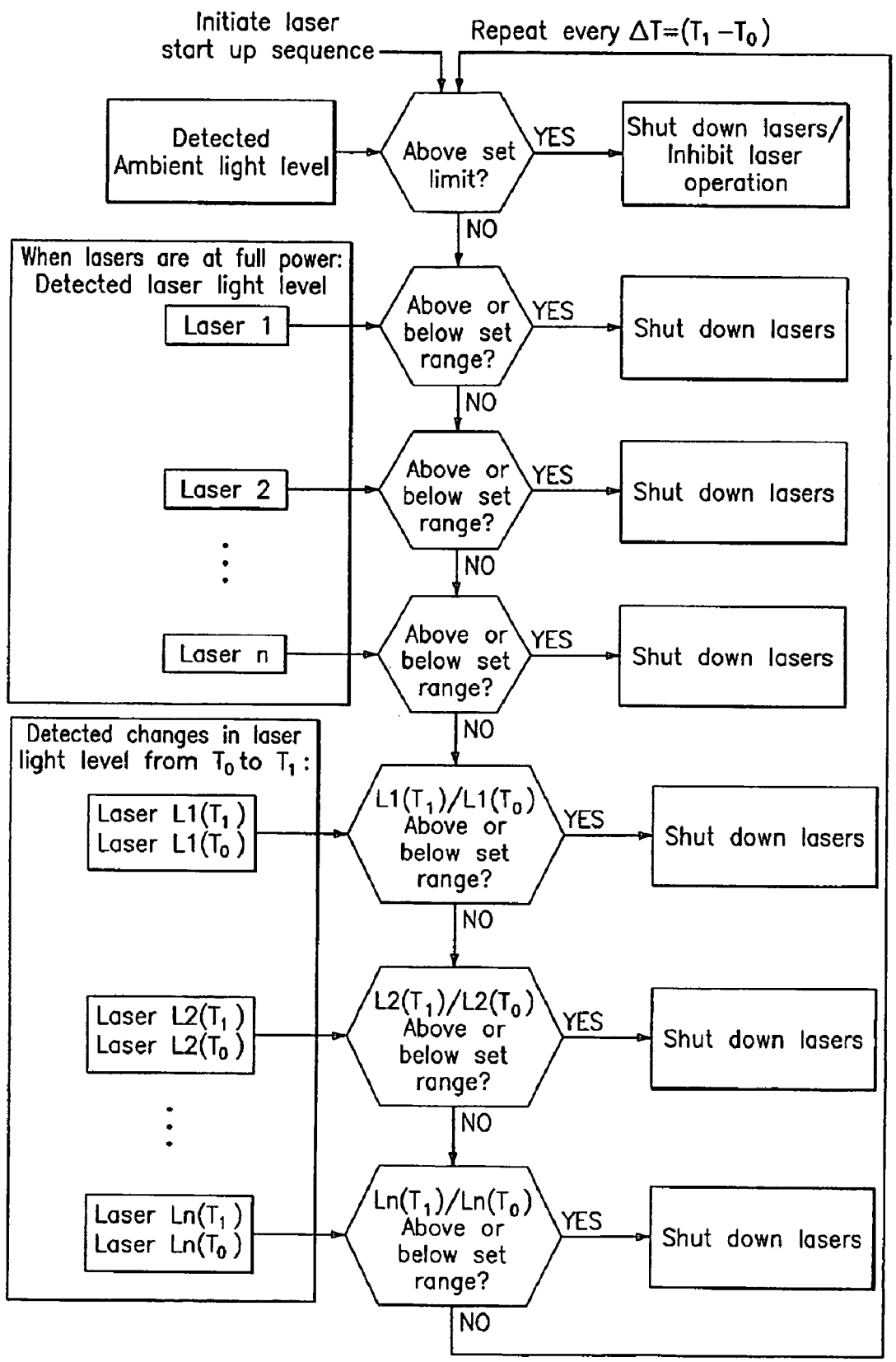
FIG. 18 shows the details of the employed laser safety interlock scheme displayed in flowchart form during normal operation of the NIRS transducer/monitor system processor.

FIG. 18 shows a flow chart that demonstrates the operation of the laser safety interlock. When the NIRS optical transducer is secured to the patient, the user will turn the lasers "ON". Before the lasers are allowed to activate, the detected ambient light is analyzed to determine if the ambient level is above or below a predetermined limit. If above the limit, then the lasers will be inhibited from operating. Otherwise, the lasers will be allowed to power up. When the lasers are at full power, the detected laser light level determined from the receiver photodiode 10 after propagation through biological tissue will be analyzed. If any of the lasers are above or below a predetermined range, then all the lasers will be shut down. Otherwise the lasers will remain active.

At a predetermined time after the detected laser intensity is initially measured at time $T_0$, the laser intensity will be re-measured at time $T_1$, and compared to the levels at $T_0$. For each laser, the detected intensity at $T_1$, will be divided by the intensity at $T_0$:

Ratio of intensity change $(I_R)$=Laser $n(T_1)$/Laser $n(T_0)$

Normally the ratio of intensity change $I_R$ will be near the value of 1. If the optical transducer is disturbed or detached, then the detected laser intensity will either increase or decrease from the time prior the disturbance. The detected intensity changes of the lasers due to a disturbed or detached transducer over time period $T_1$-$T_0$, will be greater than the detected intensity changes of the lasers due to extreme physiological changes such as a drop in tissue oxygenation. Therefore, if $I_R$ changes above or below a predetermined range over a predetermined time period $T_1$-$T_0$, then the lasers will be shut down. Otherwise the lasers will remain active.

As shown by the laser interlock flowchart, the ambient light level and laser power will be continually analyzed at the predetermined time period $\Delta T$. The sensitivity of the laser safety interlock can be adjusted by selecting the appropriate values for maximum ambient light level allowed, range of laser intensity allowed, allowable change in $I_R$ of the lasers over a period of $\Delta T$, and/or the period $\Delta T$ itself. The advantages of this laser interlock scheme are that minimal additional components are needed, and the flowchart can be implemented in software.

During optical transducer operation, low laser detected light levels would indicate that the laser light potentially is radiating in free space, or is obstructed. High detected laser light levels would indicate that the assembly is loose, by assuming that laser light is reflecting off the skin or an object to the photodiode 10, without passing through biological tissue.

For normal, daytime operation, ambient light is monitoring by measuring the low frequency component (0 to 20 Hz) of the detected light. This is obtained by low pass filtering the photodiode preamplifier output. When the ambient light detected reaches a predetermined level, indicating possible NIRS assembly detachment, laser operation is inhibited. The laser diodes 14 will not pulse until the ambient light level is below the set maximum limit, which will initially indicate secure assembly attachment during the beginning of the monitoring session. Any event that indicates assembly detachment will require user intervention to reattach the assembly 2 and to reset the laser safety interlock before laser diode pulsing can resume.

This method is an improvement by only analyzing the changes of laser intensity with one light detector, and not the ratio of the laser intensity changes from a reflection detector divided by the laser light intensity changes from an output detector over a predetermined measuring period $T_1$-$T_0$. Another improvement is that this method provides means to determine if the optical transducer is initially securely attached to the subject, before laser activation, by monitoring ambient light levels first. Then once the lasers are powered, the detected intensities of the lasers are checked to verify that they are in a predetermined range. This provides additional safety means to check to see if the lasers are operating properly and are not radiating at a power and intensity level that is too high or too low at startup or any time during a monitoring session.

Since many changes and variations of the disclosed embodiment of the invention may be made without departing from the inventive concept, it is not intended to limit the invention otherwise than as required by the appended claims.

What is claimed is:

1. An infrared spectrometric monitoring transducer, comprising:

a light source operable to produce a light signal along a plurality of discrete wavelengths, mounted in a first pod;

at least one light detector operable to receive light energy corresponding to the light signal, mounted in a second pod that is independent of the first pod;

an electromagnetic interference shielding structure shielding the at least one light detector and mounted in the second pod such that light received by the at least one light detector must pass through the electromagnetic interference shielding structure; and a light-shielding flexible member extending between the first and second pods.

2. The transducer of claim 1, wherein the transducer includes a first and a second light detector, both mounted in the second pod.

3. The transducer of claim 1, wherein the light-shielding flexible member is a cable.

* * * * *

UNITED STATES PATENT AND TRADEMARK OFFICE
CERTIFICATE OF CORRECTION

| | | |
|---|---|---|
| PATENT NO. | : 7,313,427 B2 | Page 1 of 1 |
| APPLICATION NO. | : 11/384615 | |
| DATED | : December 25, 2007 | |
| INVENTOR(S) | : Paul Benni | |

It is certified that error appears in the above-identified patent and that said Letters Patent is hereby corrected as shown below:

On the title page item (54), and col. 1, line 4, insert --Monitoring-- after "Oxygenation".

Signed and Sealed this

Twenty-ninth Day of April, 2008

JON W. DUDAS
*Director of the United States Patent and Trademark Office*